(12) United States Patent
Gill

(10) Patent No.: US 8,828,096 B2
(45) Date of Patent: Sep. 9, 2014

(54) PROSTHESIS COVERING

(75) Inventor: Hugh Gill, Livingston (GB)

(73) Assignee: Touch EMAS Limited, Livingston (GB)

( * ) Notice: Subject to any disclaimer, the term of this patent is extended or adjusted under 35 U.S.C. 154(b) by 209 days.

(21) Appl. No.: 13/139,780

(22) PCT Filed: Dec. 18, 2009

(86) PCT No.: PCT/GB2009/002919
§ 371 (c)(1),
(2), (4) Date: Aug. 9, 2011

(87) PCT Pub. No.: WO2010/070296
PCT Pub. Date: Jun. 24, 2010

(65) Prior Publication Data
US 2012/0065743 A1 Mar. 15, 2012

(30) Foreign Application Priority Data
Dec. 19, 2008 (GB) .................................. 0823228.2

(51) Int. Cl.
*A61F 2/66* (2006.01)
*A41D 19/00* (2006.01)
*A61F 2/58* (2006.01)
*A61F 2/50* (2006.01)
*A61F 2/00* (2006.01)
*A61F 2/78* (2006.01)

(52) U.S. Cl.
CPC ......... *A61F 2/583* (2013.01); *A61F 2002/5001* (2013.01); *A61F 2/0059* (2013.01); *A61F 2/78* (2013.01)
USPC .................... 623/57; 2/161.7; 2/161.8; 2/167

(58) Field of Classification Search
USPC ............... 623/57–65; 2/159, 167–168, 161.7, 2/161.8
See application file for complete search history.

(56) References Cited

U.S. PATENT DOCUMENTS

| 2,508,156 A | 5/1950 | Gillman |
| 4,960,425 A | 10/1990 | Yan et al. |
| 5,088,125 A | 2/1992 | Ansell et al. |
| 5,133,775 A | 7/1992 | Chen |

(Continued)

FOREIGN PATENT DOCUMENTS

| DE | 20315575 | 1/2004 |
| EP | 0256643 A2 | 2/1988 |

(Continued)

OTHER PUBLICATIONS

Lager, Johan, "International Search Report", for PCT/GB2009/002919, as mailed Mar. 19, 2010, 3 pages.

(Continued)

*Primary Examiner* — Bruce E Snow
(74) *Attorney, Agent, or Firm* — K&L Gates LLP

(57) ABSTRACT

The present invention relates to a covering (10) for a prosthetic hand. The covering (10) comprises a first layer (12) in the form of a glove or mitten configured to cover a prosthetic hand, with the first layer (12) comprising an elastomer. The covering (10) also comprises a second layer (14) disposed over at least part of a surface of the first layer (12), with the second layer being unitary and comprising polyurethane. At least one part of an interior surface of the first layer (12) is uncovered by the second layer (14).

22 Claims, 2 Drawing Sheets

(56) References Cited

U.S. PATENT DOCUMENTS

| | | | |
|---|---|---|---|
| 5,387,245 A | 2/1995 | Fay et al. | |
| 5,785,960 A | 7/1998 | Rigg et al. | |
| 5,852,675 A | 12/1998 | Matsuo et al. | |
| 6,111,973 A | 8/2000 | Holt et al. | |
| 6,175,962 B1 | 1/2001 | Michelson | |
| 7,316,795 B1 | 1/2008 | Knauss | |
| 2002/0016631 A1 | 2/2002 | Marchitto et al. | |
| 2005/0101693 A1 | 5/2005 | Arbogast et al. | |
| 2006/0229755 A1 | 10/2006 | Kuiken et al. | |
| 2007/0058860 A1 | 3/2007 | Harville et al. | |
| 2007/0061111 A1 | 3/2007 | Jung et al. | |
| 2007/0071314 A1 | 3/2007 | Bhatti et al. | |
| 2007/0230832 A1 | 10/2007 | Usui et al. | |
| 2008/0260218 A1 | 10/2008 | Smith et al. | |
| 2011/0203027 A1* | 8/2011 | Flather et al. | 2/48 |

FOREIGN PATENT DOCUMENTS

| | | |
|---|---|---|
| EP | 0947899 A2 | 10/1999 |
| EP | 0968695 A2 | 1/2000 |
| GB | 2067074 A | 7/1981 |
| GB | 2357725 | 4/2001 |
| GB | 2357725 | 7/2001 |
| JP | S53-94693 | 8/1978 |
| JP | 7174631 A | 7/1995 |
| JP | 2001299448 A | 10/2001 |
| JP | 2002131135 A | 5/2002 |
| JP | 2003134526 A | 5/2003 |
| JP | 2004073802 A | 3/2004 |
| WO | 96/23643 | 8/1996 |
| WO | 00/25840 | 5/2000 |
| WO | 200104838 A1 | 1/2001 |
| WO | 2003017877 A1 | 3/2003 |
| WO | 2006058190 A2 | 6/2006 |
| WO | 2006092604 A2 | 9/2006 |
| WO | WO-2006/110790 A2 | 10/2006 |
| WO | WO-2008/044052 | 4/2008 |

OTHER PUBLICATIONS

Facts and Statement of Grounds, Subject-matter of EP 2 379 018 B1, dated Nov. 18, 2013, pp. 1-7. Germany.

* cited by examiner

PROSTHESIS COVERING

FIELD OF THE INVENTION

The present invention relates to a covering for a prosthetic hand, in particular but not exclusively a covering in the form of a glove or mitten. The present invention also relates to a method of forming the same.

STATEMENT OF INVENTION

According to a first aspect of the present invention, there is provided a covering for a prosthetic hand comprising:
- a first layer in the form of a glove or mitten configured to cover a prosthetic hand, the first layer comprising an elastomer; and
- a second layer disposed over at least part of a surface of the first layer, the second layer being unitary and comprising polyurethane.

More specifically, the second layer may be disposed over at least part of an interior surface of the first layer. In use, disposing the second layer over at least part of the interior surface of the first layer may provide for ease of putting the cover on and removing the cover from a prosthetic hand. For example, it may be possible for a person with a prosthetic hand to put the cover onto his prosthetic hand using his remaining natural hand only and in less than thirty seconds. At present, isopropyl alcohol (IPA) is applied to one other or both of the covering and the prosthesis to ease the putting of the covering on to the prosthesis. Use of isopropyl alcohol can be messy.

More specifically, at least one part of the interior surface of the first layer may be uncovered by the second layer. Having at least one part of the interior surface of the first layer uncovered by the second layer may provide for improved mechanical coupling between the uncovered surface of the first layer and the prosthetic hand, e.g. on account of a tackiness of the uncovered surface.

More specifically, the interior surface of the first layer, which, in use of the covering, is adjacent at least one digit of the prosthetic hand may be uncovered. For example, the first layer may define at least one sheath for receiving at least one digit of the prosthesis and at least a portion of the interior surface of the sheath may be uncovered. Thus, there may be improved mechanical coupling between the interior surface of the covering that is uncovered by the second layer and at least one digit of the prosthetic hand. Hence, the covering may be less liable to move in relation to, e.g. may be less liable to rotate about, the at least one digit of the prosthetic hand to thereby provide for an improvement in performance of operations of the prosthetic hand involving fine motor control, e.g. such as the gripping of a pen between digits of the prosthetic hand.

More specifically, a part of the interior surface of the first layer adjacent at least a distal phalange of the prosthetic hand may be uncovered by the second layer. Thus, for example, the interior surface of the first layer adjacent the distal phalange and at least part of an intermediate phalange of the prosthetic hand may be uncovered.

Where the first layer is in the form of a glove defining a plurality of sheaths for covering respective individual digits of a prosthetic hand, at least a part of at least one sheath other than a sheath for a thumb of the prosthetic hand may be uncovered by the second layer.

Alternatively or in addition, at least a part of a palm area of the interior surface of the first layer may be uncovered. Thus, there may be improved mechanical coupling between the palm area of the covering and the palm of the prosthetic hand to thereby provide for an improvement in performance of operations of the prosthetic hand involving gripping of objects by the prosthetic hand, such as the gripping of a mug between digits and the palm area of the prosthetic hand.

Alternatively or in addition, the second layer may be disposed over a part of a surface of the first layer at a plurality of spaced apart locations. Where the second layer is disposed over the surface, e.g. the interior surface, of the first layer at a plurality of spaced apart locations the second layer is unitary at each of the spaced apart locations.

Alternatively or in addition, the second layer may be disposed over at least part of an exterior surface of the first layer.

More specifically, the second layer may be disposed on an exterior surface of the first layer solely over at least one of: the back of the hand (i.e. the dorsal surface); the wrist adjacent the back of the hand; and the side of the hand. Thus, the presence of the second layer over at least one of the back of the hand the wrist and the side of the hand may provide a comparatively low friction surface so that a prosthetic hand bearing the covering may pass more readily through a sleeve of clothing. The absence of the second layer on other parts of the exterior surface of the covering, in particular the front of the hand, which is defined by the palm and surfaces of the sheaths extending from the palm (i.e. the palmar surface), which receive prosthetic digits, may provide a comparatively higher friction surface. Such a comparatively higher friction surface or a tackiness of the uncoated surface may provide for improved grip of objects by a prosthetic hand having the covering of the present invention.

Alternatively or in addition, the second layer may define an exposed surface facing away from the first layer, the exposed surface having a surface roughness of between substantially 15 and substantially 25 according to the VDI, EDM scale.

More specifically, the exposed surface may have a surface roughness of substantially 20 according to the VDI, EDM scale.

Alternatively or in addition, the first layer may be unitary.

Alternatively or in addition, the elastomer of the first layer may define a furthest extent of the first layer.

Alternatively or in addition, the elastomer may be a thermoplastic elastomer.

Alternatively or in addition, the elastomer may comprise a silicone rubber. The silicone rubber may be high temperature vulcanised (HTV) silicone rubber. In a form of the invention, the first layer may consist substantially of an elastomer, such as silicone rubber.

In another form of the invention, the first layer may comprise a textile substrate. The elastomer of the first layer may be attached to the textile substrate.

More specifically, the elastomer of the first layer may be disposed substantially on an exterior surface of the covering. Thus, there may be no or very little elastomer present at the interior surface of the textile substrate.

Alternatively, the textile substrate may be embedded in the elastomer of the first layer.

Alternatively or in addition, the textile substrate may comprise a spandex material, such as Lycra™. More specifically, the textile substrate may comprise substantially 4% Lycra™ to substantially 12% Lycra™.

Alternatively or in addition, the second layer may be attached to a surface of the first layer.

Alternatively or in addition, the second layer may consist substantially of polyurethane.

Alternatively or in addition, the second layer may be a film of material on the first layer.

Alternatively or in addition, the second layer may comprise polyurethane resin, crosslink agent and filler. In forms of the invention, the second layer may consist of substantially 82.4% polyurethane resin, substantially 3.5% crosslink agent and substantially 14.1% filler.

Alternatively or in addition, the second layer may comprise a pigment. Thus, the covering may be coloured, e.g. the covering may be black or flesh coloured.

Alternatively or in addition, the first layer may have a thickness from interior surface to exterior surface of between substantially 0.5 mm and substantially 2 mm.

More specifically, the first layer may have a thickness of substantially 1.5 mm.

According to a second aspect of the present invention, there is provided a prosthetic hand comprising a covering according to the first aspect of the present invention.

Embodiments of the second aspect of the present invention may comprise one or more features of the first aspect of the present invention.

According to a third aspect of the present invention, there is provided a method of forming a covering for a prosthetic hand, the method comprising:
  forming a first layer such that the first layer has the form of a glove or a mitten that is configured to cover a prosthetic hand, the first layer comprising an elastomer; and
  disposing a second layer over at least part of a surface of the first layer, the second layer being unitary and comprising polyurethane.

More specifically, the first layer may be formed by at least one of: a compression moulding process; and a liquid injection moulding process.

Alternatively or in addition, the method may further comprise polishing a tool on which the first layer is formed to a mirror finish. Forming the first layer on a tool polished to a mirror finish may provide a correspondingly smooth finish on a surface of the first layer. An elastomer having a smooth finish may provide for high static friction threshold.

Alternatively or in addition, disposing the second layer may comprise disposing a film of material, e.g. a liquid, on the first layer.

More specifically, disposing the second layer may comprise spraying the material onto the first layer, the material comprising polyurethane dissolved in toluene.

More specifically, the sprayed material may consist of may consist of substantially 70% polyurethane resin, substantially 15% toluene, substantially 3% crosslink agent and substantially 12% filler.

Alternatively or in addition, the method may comprise heating the covering after deposition of the second layer on the first layer.

According to a further aspect of the present invention, there is provided a covering for a prosthesis comprising:
  a first layer configured to cover the prosthesis, the first layer comprising an elastomer; and
  a second layer disposed over at least part of a surface of the first layer, the second layer being unitary and comprising polyurethane.

More specifically, the first layer may have a general form of the prosthesis to be covered. For example, where the prosthesis is a hand the first layer may be in the form of a glove or mitten or where the prosthesis is in the form of a foot the covering may be in form of a sock.

Further embodiments of the further aspect of the present invention may comprise one or more features of any previous aspect of the present invention.

BRIEF DESCRIPTION OF THE DRAWINGS

The present invention will now be described by way of example only with reference to the following drawings, of which.

SPECIFIC DESCRIPTION

Figure 1:
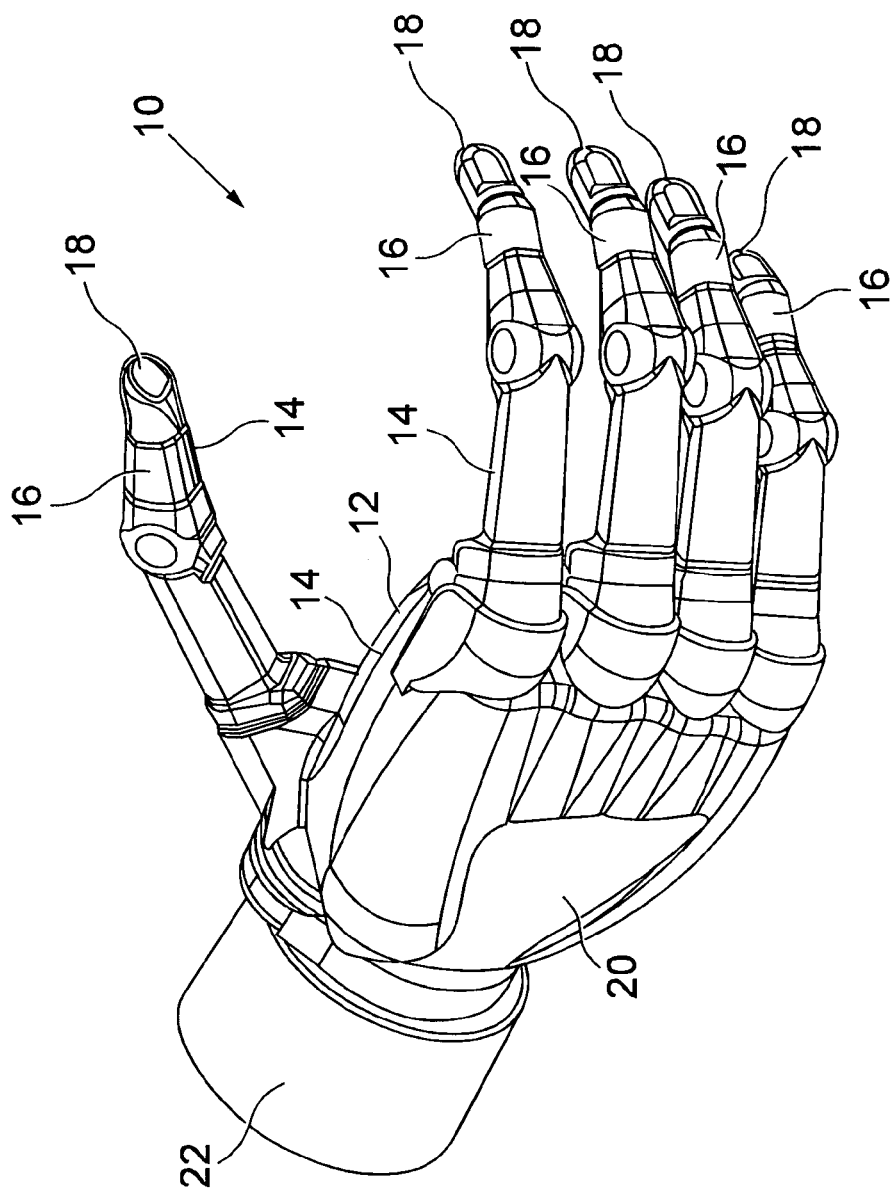
FIG. 1 is a perspective view of a covering for a prosthetic hand according to the present invention.

FIG. 1 provides a perspective view of a covering 10 according to the present invention. The covering comprises a first layer 12 formed substantially of high temperature vulcanised (HTV) silicone rubber, such as Elastosil® R 401/20-R 401/90 from Wacker-Chemie GmbH of Geschaftsbereich Silicone, Hanns-Seidel-Platz 4, D-81737 Munich. The covering also comprises a film of polyurethane 14 (which constitutes a second layer). The film of polyurethane consists of substantially 82.4% polyurethane resin, substantially 3.5% crosslink agent and substantially 14.1% filler from General Silicones Company Limited of The 6$^{th}$ Industrial Zone of Liwa Washa Village, Changan Town, Dongguan City, Guangdong Province, China. The polyurethane 14 is on parts of the surface of the first layer 12 as follows.

The entire interior surface of the first layer is covered with the polyurethane 14 with the exception of the interior surface of parts of the sheaths of the covering that receive the digits of a prosthetic hand. More specifically, an area of the interior surface of each sheath from the tip of the sheath 18, over the area corresponding to the distal phalange 16 and along part of the area corresponding to the intermediate phalange 16 are uncovered by the polyurethane 14. Also, the palm area of the interior surface of the covering is uncovered by polyurethane 14.

The entire exterior surface of the first layer 12 is uncovered with polyurethane 14 with the exception of an area on the back of the hand 20, an area on the wrist 22 and the sides of the hand. Covering the exterior surface in this fashion provides a low friction surface that allows a prosthetic hand bearing the covering to pass more readily through a sleeve of clothing.

In an alternative embodiment of the present invention, the first layer comprises a textile substrate, which is embedded in the high temperature vulcanised silicone rubber. Thus, this embodiment appears substantially as shown in FIG. 1. The textile layer is formed of 92% nylon and 8% Lycra™. The nylon and Lycra are woven with a pitch of substantially 591 needles per meter. Other details as regards the form of the textile and the silicone rubber and of the composition of the textile are as described in WO 2008/044052. This first layer of this embodiment is coated with polyurethane as described above in the immediately preceding two paragraphs.

Figure 2:
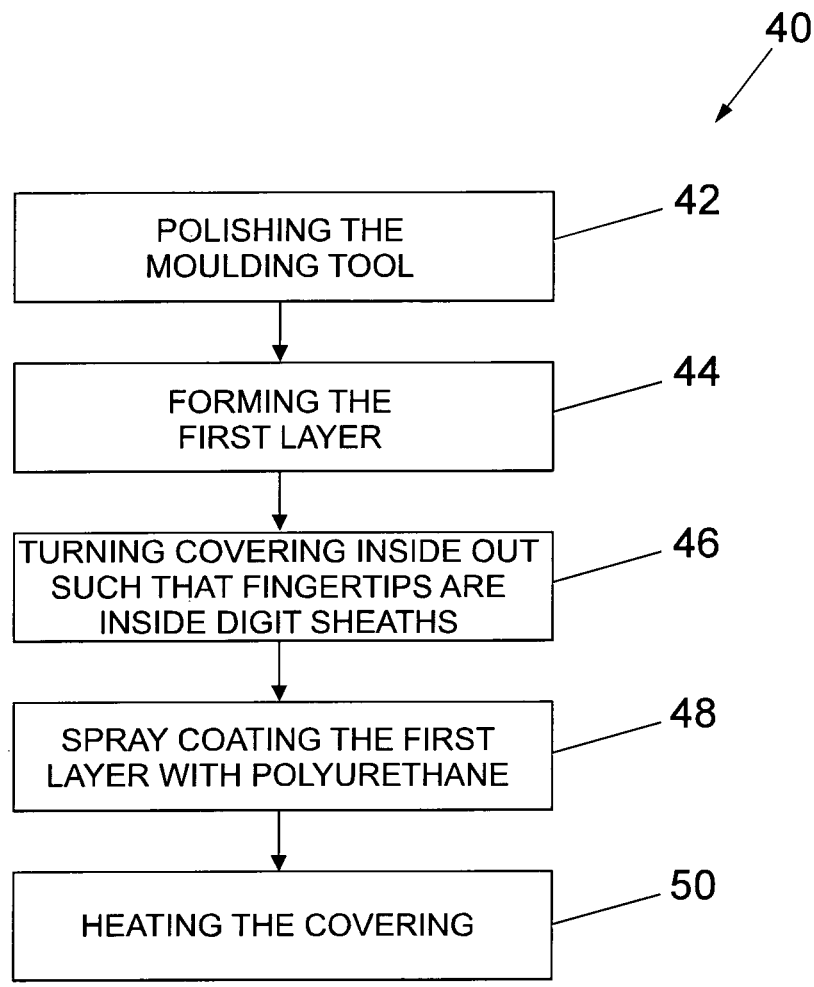
FIG. 2 is a flow chart representation of a method of forming the covering of FIG. 1.

A method of forming the covering will now be described with reference to the flow chart 40 of FIG. 2. The moulding tool, which is to be used in the forming of the first layer, is polished to a high finish 42. Then the moulding tool is used to form the first layer by either compression moulding or liquid injection moulding 44. The compression moulding and liquid injection moulding processes are as described in detail at www.kdlprecision.com/moldtype.htm. When the formed first layer has cured properly, the first layer is turned inside out 46. Then the tips of the digit sheaths are pushed back into their respective sheaths such that the portions that are to remain uncovered by polyurethane are folded back within their respective sheaths 46. The exposed interior surface of the first layer is spray coated with liquid polyurethane mixture 48, the polyurethane having been dissolved in toluene. The liquid polyurethane mixture consists of substantially 70% polyurethane resin, substantially 15% toluene, substantially 3% crosslink agent and substantially 12% filler. After spray coating, the covering is placed in an oven and heated to drive off the solvent and cure the polyurethane coating. The covering is then reversed such that the interior surface is disposed towards the inside of the covering. The back of the hand and wrist area of the exterior surface are then spray coated with liquid polyurethane, the areas to remain uncovered having been masked. The covering is then placed in an oven and heated to drive off the solvent from the liquid polyurethane and cure the polyurethane coating on the exterior surface of the covering.

The forming process for the second embodiment is the same as described above in respect of the deposition of the polyurethane film as described above. The formation of the first layer is as described in detail in WO 2008/044052.

The invention claimed is:

1. A covering for a prosthetic hand comprising:
   a first layer in the form of a glove or mitten configured to cover a prosthetic hand, the first layer comprising an elastomer; and
   a second layer disposed over at least part of an interior surface of the first layer, the second layer being unitary and comprising polyurethane, at least a finger portion of the interior surface of the first layer being uncovered by the second layer,
   wherein the second layer provides a reduced friction surface between the prosthetic hand and second layer.

2. A covering according to claim 1, wherein a part of the interior surface of the first layer, which, in use of the covering, is adjacent at least one digit of the prosthetic hand is uncovered.

3. A covering according to claim 2, wherein a part of the interior surface of the first layer adjacent at least a distal phalange of the prosthetic hand is uncovered by the second layer.

4. A covering according to claim 1, wherein the first layer is in the form of a glove defining a plurality of sheaths for covering respective individual digits of a prosthetic hand, at least a part of an internal surface of at least one sheath other than a sheath for a thumb of the prosthetic hand is uncovered by the second layer.

5. A covering according to claim 1, wherein at least a part of a palm area of the interior surface of the first layer is uncovered by the second layer.

6. A covering according to claim 1, wherein the second layer is disposed over a part of a surface of the first layer at a plurality of spaced apart locations.

7. A covering according to claim 6, wherein the second layer is unitary at each of the spaced apart locations.

8. A covering according to claim 1, wherein the second layer is disposed on an exterior surface of the first layer solely over at least one of: the back of the hand; the wrist adjacent the back of the hand; and the side of the hand.

9. A covering according to claim 1, wherein the second layer defines an exposed surface facing away from the first layer, the exposed surface having a surface roughness of between substantially 15 and substantially 25 according to the VDI, EDM scale.

10. A covering according to claim 1, wherein the first layer is unitary and the elastomer defines a furthest extent of the first layer.

11. A covering according to claim 1, wherein the elastomer is a thermoplastic elastomer.

12. A covering according to claim 11, wherein the elastomer comprises a high temperature vulcanised (HTV) silicone rubber.

13. A covering according to claim 1, wherein the first layer comprises a textile substrate.

14. A covering according to claim 13, wherein the elastomer of the first layer is attached to the textile substrate.

15. A covering according to claim 14, wherein the elastomer of the first layer is one of: disposed substantially on an exterior surface of the covering; and embedded in the elastomer of the first layer.

16. A covering according to claim 13, wherein the textile substrate comprises a spandex material.

17. A covering according to claim 1, wherein the second layer is attached to a surface of the first layer.

18. A covering according to claim 1, wherein the second layer is a film of material on the first layer.

19. A covering according to claim 1, wherein the second layer comprises polyurethane resin, crosslink agent and filler.

20. A covering according to claim 1, wherein the second layer comprises a pigment.

21. A covering according to claim 1, wherein the first layer has a thickness from interior surface to exterior surface of between substantially 0.5 mm and substantially 2 mm.

22. A prosthetic hand comprising a mechanical hand and a covering constructed according to claim 1.

* * * * *